United States Patent
Birch et al.

[11] Patent Number: 6,107,310
[45] Date of Patent: Aug. 22, 2000

[54] HETEROARYLCARBOXAMIDE DERIVATIVES FOR TREATING CNS DISORDERS

[75] Inventors: Alan Martin Birch; Paul Anthony Bradley; Julie Carolyn Gill, all of Nottingham, United Kingdom

[73] Assignee: Knoll Aktiengesellschaft, Ludwigshafen, Germany

[21] Appl. No.: 09/091,129

[22] PCT Filed: Dec. 16, 1996

[86] PCT No.: PCT/EP96/05637

§ 371 Date: Jun. 16, 1998

§ 102(e) Date: Jun. 16, 1998

[87] PCT Pub. No.: WO97/23485

PCT Pub. Date: Jul. 3, 1997

[30] Foreign Application Priority Data

Dec. 23, 1995 [GB] United Kingdom .................. 9526495

[51] Int. Cl.[7] ........................ A61K 31/445; C07D 401/14
[52] U.S. Cl. ........................ 514/318; 514/321; 514/322; 546/193; 546/197; 546/199
[58] Field of Search ..................... 514/318, 321, 514/322; 546/193, 197, 199

[56] References Cited

U.S. PATENT DOCUMENTS 5,302,599  4/1994  Ennis ........................ 514/278

FOREIGN PATENT DOCUMENTS

| 58-154574 | 9/1983 | Japan . |
| 91/13872 | 9/1991 | WIPO . |
| 95/07274 | 3/1995 | WIPO . |

OTHER PUBLICATIONS

Rubini et al. "Synthesis of isosteric methylene oxy . . . " Tetrahedron v. 42, pp. 6039–6045, 1986.

Primary Examiner—Ceila Chang
Attorney, Agent, or Firm—Keil & Weinkauf

[57] ABSTRACT

Compounds of formula I

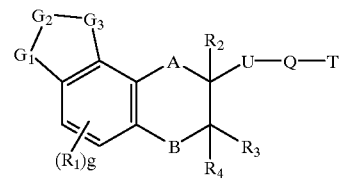

and pharmaceutically acceptable salts thereof in which A is methylene or —O—; B is methylene or —O—; $G_1$—$G_2$—$G_3$ are absent or form a heteroaromatic chain; g is 0,1,2,3 or 4; U is an alkylene chain optionally substituted by one or more alkyl; Q represents a divalent group containing nitrogen atoms; and T represents CO. HET, have utility in the treatment of central nervous system disorders, for example depression, anxiety, psychoses (for example schizophrenia), tardive dyskinesia, Parkinson's disease, obesity, hypertension, Tourette's syndrome, sexual dysfunction, drug addiction, drug abuse, cognitive disorders, Alzheimer's disease, senile dementia, obsessive-compulsive behaviour, panic attacks, social phobias, eating disorders and anorexia, cardiovascular and cerebrovascular disorders, non-insulin dependent diabetes mrellitus, hyperglvcaemia, constipation, arrhythmia, disorders of the neuroendocrine system, stress, prostatic hypertrophy, and spasticity.

23 Claims, No Drawings

HETEROARYLCARBOXAMIDE DERIVATIVES FOR TREATING CNS DISORDERS

This is a 371 of PCT/EP96/05637 filed Dec. 16, 1996.

The present invention relates to novel heteroarylcarboxamide compounds which have affinity for 5-HT$_{1A}$ and/or $\alpha_1$, and/or D$_2$-like (D$_2$, D$_3$ and D$_4$ sub-types) receptors, to processes for their preparation, to pharmaceutical compositions containing them and to their use in the treatment of central nervous system disorders, for example depression, anxiety, psychoses (for example schizophrenia), tardive dyskinesia, Parkinson's disease, obesity, hypertension, Tourette's syndrome, sexual dysfunction, drug addiction, drug abuse, cognitive disorders, Alzheimer's disease, senile dementia, obsessive-compulsive behaviour, panic attacks, social phobias, eating disorders and anorexia, cardiovascular and cerebrovascular disorders, non-insulin dependent diabetes mellitus, hyperglycaemia, constipation, arrhythmia, disorders of the neuroendocrine system, stress, prostatic hypertrophy, and spasticity.

The present invention provides compounds of formula I

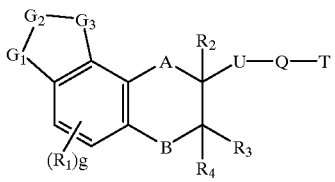

I including enantiomers and pharmaceutically acceptable salts thereof in which

A is methylene or —O—;

B is methylene or —O—;

G$_1$—G$_2$—G$_3$ represent —N(R')—C(R")=N—, —N=C(R")—N(R')—, —N(R')—C(R")=C(R''')—, —C(R''')=C(R")—N(R')—, —N(R')—N=C(R")—, —C(R")=N—N(R')—, —N(R')—N=N—, —N=N—N(R')—, —N=C(R")—O—, —N=C(R")—S—, —O—C(R")=N—, —S—C(R")=N—, —O—N=C(R")—, —S—N=C(R")—, —C(R")=N—O—, —C(R")=N—S—, —S—C(R")=C(R''')—, —C(R''')=C(R")—S—, —O—C(R")=C(R''')—, or —C(R")=C(R''')—O—;

R' is H or an alkyl group containing 1 to 3 carbon atoms;

R" and R''', which are the same or different, are H; halo; an alkyl group containing 1 to 3 carbon atoms optionally substituted by one or more halo; carboxy; an alkanoyl group containing 1 to 6 carbon atoms; an alkoxycarbonyl group in which the alkoxy group contains 1 to 3 carbon atoms; formyl; cyano; or a carbamoyl group or carbamoylmethyl group each optionally N-substituted by one or two alkyl groups, which may be the same or different, each containing 1 to 3 carbon atoms;

g is 0, 1 or 2;

R$_1$ represents an alkyl group containing 1 to 3 carbon atoms optionally substituted by one or more halo; an alkoxy group containing 1 to 3 carbon atoms optionally substituted by one or more halo; halo; or an alkylthio group containing 1 to 3 carbon atoms optionally substituted by one or more halo; the substituents represented by R$_1$ being the same or different when g is 2;

R$_2$ is H, an alkyl group containing 1 to 3 carbon atoms, or an alkoxy group containing 1 to 3 carbon atoms;

R$_3$ and R$_4$, which are the same or different, are H, or an alkyl group containing 1 to 3 carbon atoms;

U is an alkylene chain containing 1 to 3 carbon atoms, optionally substituted by one or more alkyl groups each containing 1 to 3 carbon atoms;

Q represents a divalent group of formula IIa, IIb or IIc

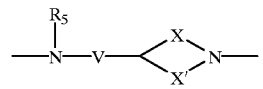

IIa

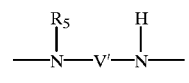

IIb

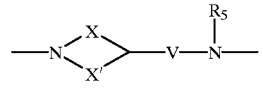

IIc in which V is a bond or an alkylene chain containing 1 to 3 carbon atoms optionally substituted by one or more alkyl groups each containing 1 to 3 carbon atoms;

V' is an alkylene chain containing 2 to 6 carbon atoms, optionally substituted by one or more alkyl groups each containing 1 to 3 carbon atoms;

X is an alkylene chain containing 0 to 2 carbon atoms and X' is an alkylene chain containing 1 to 4 carbon atoms provided that the total number of carbon atoms in X and X' amounts to 3 or 4; R$_5$ is H or an alkyl group containing 1 to 3 carbon atoms; and T represents the group CO.HET in which HET is 2-, 3- or 4-pyridyl, 2-, 4- or 5-pyrimidinyl, 2- or 3-thienyl, 2- or 3-furyl, 2-, 3- or 7-benzo[b]furanyl, 2,3-dihydro-7-benzo[b]furanyl, 2-, 3- or 7-benzo[b]thiophenyl, 2- or 3-piperidyl, 3-, 4- or 5-4- or 5-triazolyl, 5-tetrazolyl, 2-, 3- or 4-quinolinyl, 2- or 4-quinazolinyl, 3-, 4- or 5-isoxazolyl, 2-, 4- or 5-oxazolyl, 3-, 4- or 5-isothiazolyl or 2-, 4- or 5-thiazolyl each which may be optionally substituted by one or more substituents selected from a) halo, b) an alkyl group containing 1 to 3 carbon atoms optionally substituted by one or more halo, c) an alkoxy group containing 1 to 3 carbon atoms optionally substituted by one or more halo, d) an alkylthio group containing 1 to 3 carbon atoms optionally substituted by one or more halo, e) hydroxy, f) an acyloxy group containing 1 to 3 carbon atoms, g) hydroxymethyl, h) cyano, i) an alkanoyl group containing 1 to 6 carbon atoms, j) an alkoxycarbonyl group containing 2 to 6 carbon atoms, k) a carbamoyl group or carbamoylmethyl group each optionally N-substituted by one or two alkyl groups each containing 1 to 3 carbon atoms, I) a sulphamoyl or sulphamoylmethyl group each optionally N-substituted by one or two alkyl groups each containing 1 to 3 carbon atoms, m) an amino group optionally substituted by one or two alkyl groups each containing 1 to 5 carbon atoms, or n) 1-pyrrolidinyl or 1-piperidinyl.

In preferred compounds of formula I, A is —O—.

In preferred compounds of formula I, B is —O—.

In more preferred compounds of formula I, both A and B are —O—.

In preferred compounds of formula I, g is 0 or 1. When g is 1, R$_1$ is preferably halo or an alkyl group containing 1 to 3 carbon atoms.

In preferred compounds of formula I, G$_1$—G$_2$—G$_3$ are —NH—CH=CH—.

In preferred compounds of formula I, $R_2$ is H or an alkyl group containing 1 to 3 carbon atoms. In more preferred compounds of formula I, $R_2$ is H.

In preferred compounds of formula I, $R_3$ and $R_4$, which are the same or different, are H or methyl. In more preferred compounds of formula I, $R_3$ and $R_4$ are both H.

In preferred compounds of formula I, U is methylene.

In preferred compounds of formula I, in which Q is a group of formula IIa or IIc, V is methylene or ethylene.

In preferred compounds of formula I, in which Q is a group of formula IIb, V' is an alkylene chain containing 2 to 4 carbon atoms.

In more preferred compounds of formula I, Q is a group of formula IIc in which X and X' are both ethylene, and V is methylene.

In preferred compounds of formula I, $R_5$ is H or methyl. In more preferred compounds of formula I, $R_5$ is H.

In preferred compounds of formula I, T is the group CO.HET in which HET is 2-, 3- or 4-pyridyl optionally substituted by one or more substituents selected from methoxy, trifluoromethyl, halo or an amino group optionally substitued by one or two alkyl groups each containing 1 to 3 carbon atoms. In more preferred compounds of formula I in which T is CO.HET, HET is 3-pyridyl substituted by an amino group, or 2-pyridyl.

In a group of preferred compounds of formula I, $G_1$—$G_2$—$G_3$ are —NH—C(R")=CH—, —NH—N=CH— or —NH—CH=N—; R" is H, $CO_2Et$, $CONH_2$, $CONMe_2$, COMe, CN, or CHO; A and B are both —O—; g is 0; $R_2$, $R_3$ and $R_4$ are all H; U is methylene; Q is a group of formula IIa or IIc in which V is methylene and X and X' are both ethylene; and T is the group CO.HET in which HET is 2-pyridyl, 3-pyridyl, 3-(2-amino)pyridyl, or 3-(2-methoxy)pyridyl.

Compounds of formula I may exist as salts with pharmaceutically acceptable acids. Examples of such salts include hydrochlorides, hydrobromides, sulphates, methanesulphonates, nitrates, maleates, acetates, citrates, fumarates, tartrates [eg (+)-tartrates, (−)-tartrates or mixtures thereof including racemic mixtures], succinates, benzoates and salts with amino acids such as glutamic acid. Compounds of formula I and their salts may exist in the form of solvates (for example hydrates).

Compounds of formula I and intermediates in their preparation contain one or more chiral centres, and exist in different optically active forms. When compounds of formula I and intermediates in their preparation contain one chiral centre, the compounds exist in two enantiomeric forms and the present invention includes both enantiomers and mixtures of enantiomers. The enantiomers may be resolved by methods known to those skilled in the art, for example by formation of diastereoisomeric salts which may be separated, for example, by crystallisation; formation of diastereoisomeric derivatives or complexes which may be separated, for example, by crystallisation, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomers may be synthesised by asymmetric synthesis using optically active reagents, substrates, catalysts or solvents, or by converting one enantiomer into the other by asymmetric transformation.

When a compound of formula I contains more than one chiral centre it may exist in diastereoisomeric forms. The diastereoisomeric pairs may be separated by methods known to this skilled in the art, for example chromatography or crystallisation and the individual enantiomers within each pair may be separated as described above. The present invention includes each diastereoisomer of compounds of formula I and mixtures thereof.

Certain compounds of formula I and their salts may exist in more than one crystal form and the present invention includes each crystal form and mixtures thereof. Certain compounds of formula I and their salts may also exist in the form of solvates, for example hydrates, and the present invention includes each solvate and mixtures thereof.

Specific compounds of formula I are:

2-Amino-N-{[1-(2,3-dihydro-7H-1,4-dioxino[2,3-e]indol-2-ylmethyl)-4-piperidyl]methyl}-pyridine-3-carboxamide;

N{[1-(2,3-dihydro-7H-1,4-dioxino[2,3-e]indol-2-ylmethyl)-4-piperidyl]methyl}pyridin-2-carboxamide;

Ethyl 2,3-dihydro-2-({4-[(2-pyridinecarboxamido)methyl]piperidino}methyl)-7H-1,4-dioxino[2,3-e]indole-8-carboxylate;

Ethyl 2,3-dihydro-2-({4-[(3-pyridinecarboxamido)methyl]piperidino}methyl)-7H-1,4-dioxino[2,3-e]indole-8-carboxylate;

Ethyl 2-({4-[(2-amino-3-pyridinecarboxamido)methyl]piperidino}methyl)-2,3-dihydro-7H-1,4-dioxino[2,3-e]indole-8-carboxylate;

2,3-Dihydro-2-({4-[(2-pyridinecarboxamido)methyl]piperidino}methyl)-7H-1,4-dioxino-[2,3-e]indole-8-carboxamide;

2,3-Dihydro-2-({4-[(3-pyridinecarboxamido)methyl]piperidino}methyl)-7 H-1,4-dioxino-[2,3-e]indole-8-carboxamide;

2-({4-[(2-Amino-3-pyridinecarboxamido)methyl]piperidino}methyl)-2,3-dihydro-7H-1,4-dioxino[2,3-e]indole-8-carboxamide;

2,3-Dihydro-N,N-dimethyl-2-({4-[(2-pyridinecarboxamido)methy]piperidino}methyl)-7H-1,4-dioxino[2,3-e]indole-8-carboxamide;

2,3-Dihydro-N,N-dimethyl-2-({4-[(3-pyridinecarboxamido)methyl]piperidino}methyl)-7H-1,4-dioxino[2,3-e]indole-8-carboxamide;

2-({4-[(2-Amino-3-pyridinecarboxamido)methyl]piperidino}methyl)-2,3-dihydro-N,N-dimethyl-7H-1,4-dioxino[2,3-e]indole-8-carboxamide;

N-{[1-(8-Acetyl-2,3-dihydro-7H-1,4-dioxino[2,3-e]indol-2-ylmethyl)-4-piperidyl]-methyl}pyridine-2-carboxamide;

N-{[1-(8-Acetyl-2,3-dihydro-7H-1,4-dioxino[2,3-e]indol-2-ylmethyl)-4-piperidyl]-methyl}pyridine-3-carboxamide;

N-{[1-(8-Acetyl-2,3-dihydro-7H-1,4-dioxino[2,3-e]indol-2-ylmethyl)-4-piperidyl]-methyl}-2-aminopyridine-3-carboxamide;

N-{[1-(8-Cyano-2,3-dihydro-7H-1,4-dioxino[2,3-e]indol-2-ylmethyl)-4-piperidyl]-methyl}pyridine-2-carboxamide;

N-{[1-(8-Cyano-2,3-dihydro-7H-1,4-dioxino[2,3-e]indol-2-ylmethyl)-4-piperidyl]-methyl}pyridine-3-carboxamide;

2-Amino-N-{[1-(8-cyano-2,3-dihydro-7H-1,4-dioxino[2,3-e]indol-2-ylmethyl)-4-piperidyl]methyl}pyridine-3-carboxamide;

N-{[1-(8-Formyl-2,3-dihydro-7H-1,4-dioxino[2,3-e]indol-2-ylmethyl)-4-piperidyl]-methyl}pyridine-2-carboxamide;

N-{[1-(8-Formyl-2,3-dihydro-7H-1,4-dioxino[2,3-e]indol-2-ylmethyl)-4-piperidy]-methyl}pyridine-3-carboxamide;

2-Amino-N-{[1-(8-formyl-2,3-dihydro-7H-1,4-dioxino[2,3-e]indol-2-ylmethyl)-4-piperidyl]methyl}pyridine-3-carboxamide;

N-{[1-(2,3-Dihydro-7H-1,4-dioxino[2,3-e]indol-2-ylmethyl)-4-piperidyl]methyl}-2-methoxypyridine-3-carboxamide;

N-{[1-(2,3-Dihydro-7H-1,4-dioxino[2,3-e]indazol-2-yimethyl)-4-piperidyl]methyl}-pyridine-2-carboxamide;

N-{[1-(2,3-Dihydro-7H-1,4-dioxino[2,3-e]indazol-2-ylmethyl)-4-piperidyl]methyl}-pyridine-3-carboxamide;

2-Amino-N-{[1-(2,3-dihydro-7H-1,4-dioxino[2,3-e]indazol-2-ylmethyl)-4-piperidyl]-methyl}pyridine-3-carboxamide;

N-{[1-(2,3-Dihydro-7H-1,4-dioxino[2,3-e]benzimidazol-2-ylmethyl)-4-piperidyl]-methyl}pyridine-2-carboxamide;

-{[1-(2,3-Dihydro-7H-1,4-dioxino[2,3-e]benzimidazol-2-ylmethyl)-4-piperidyl]-methyl}pyridine-3-carboxamide;

2-Amino-N-{[1-(2,3-dihydro-7H-1,4-dioxino[2,3-e]benzimidazol-2-ylmethyl)-4-piperidyl]methyl}pyridine-3-carboxamide;

2,3-Dihydro-2-(N-{[1-(2-pyridylcarbonyl)-4-piperidyl]methyl}aminomethyl)-7H-1,4-dioxino[2,3-e]indole;

2,3-Dihydro-2-(N-{[1-(3-pyridylcarbonyl)-4-piperidyl]methyl}aminomethyl)-7H-1,4-dioxino[2,3-e]indole;

2-(N-{[1-(2-Choro-3-pyridylcarbonyl)-4-piperidyl]methyl}aminomethyl)-2,3-dihydro-7H-1,4-dioxino[2,3-e]indole;

2-(N-{[1-(2-Amino-3-pyridylcarbonyl)-4-piperidyl]methyl}aminomethyl)-2,3-dihydro-7H-1,4-dioxino[2,3-e]indole;

and pharmaceutically acceptable salts thereof in the form of individual enantiomers, racemates, or other mixtures of enantiomers.

Specific enantiomeric forms of compounds of formula I include:

(S)-2-Amino-N-{[1-(2,3-dihydro-7H-1,4-dioxino[2,3-e]indol-2-ylmethyl)-4-piperidyl]-methyl}-pyridine-3-carboxamide; and (S)-N-{[1-(2,3-dihydro-7H-1,4-dioxino[2,3-e]indol-2-ylmethyl)-4-piperidyl]methyl}-pyridine-2-carboxamide;

and pharmaceutically acceptable salts thereof.

The present invention also includes pharmaceutical compositions containing a therapeutically effective amount of a compound of formula I or a salt thereof together with a pharmaceutically acceptable diluent or carrier.

As used hereinafter, the term "active compound" denotes a compound of formula I or a salt thereof. In therapeutic use, the active compound may be administered orally, rectally, parenterally or topically, preferably orally. Thus the therapeutic compositions of the present invention may take the form of any of the known pharmaceutical compositions for oral, rectal, parenteral or topical administration. Pharmaceutically acceptable carriers suitable for use in such compositions are well known in the art of pharmacy. The compositions of the invention may contain 0.1–99% by weight of active compound. The compositions of the invention are generally prepared in unit dosage form. Preferably the unit dosage of active ingredient is 1–500 mg. The excipients used in the preparation of these compositions are the excipients known in the pharmacist's art.

Compositions for oral administration are the preferred compositions of the invention and these are the known pharmaceutical forms for such administration, for example tablets, capsules, syrups and aqueous or oil suspensions. The excipients used in the preparation of these compositions are the excipients known in the pharmacist's art. Tablets may be prepared by mixing the active compound with an inert diluent such as calcium phosphate in the presence of disintegrating agents, for example maize starch, and lubricating agents, for example magnesium stearate, and tableting the mixture by known methods. The tablets may be formulated in a manner known to those skilled in the art so as to give a sustained release of the compounds of the present invention. Such tablets may, if desired, be provided with enteric coatings by known methods, for example by the use of cellulose acetate phthalate. Similarly, capsules, for example hard or soft gelatin capsules, containing the active compound with or without added excipients, may be prepared by conventional means and, if desired, provided with enteric coatings in a known manner. The tablets and capsules may conveniently each contain 1 to 500 mg of the active compound. Other compositions for oral administration include, for example, aqueous suspensions containing the active compound in an aqueous medium in the presence of a non-toxic suspending agent such as sodium carboxymethylcellulose, and oily suspensions containing a compound of the present invention in a suitable vegetable oil, for example arachis oil.

The active compound may be formulated into granules with or without additional excipients. The granules may be ingested directly by the patient or they may be added to a suitable liquid carrier (for example water) before ingestion. The granules may contain disintegrants (for example a pharmaceutically acceptable effervescent couple formed from an acid and a carbonate or bicarbonate salt) to facilitate dispersion in the liquid medium.

Compositions of the invention suitable for rectal administration are the known pharmaceutical forms for such administration, for example, suppositories with cocoa butter or polyethylene glycol bases.

Compositions of the invention suitable for parenteral administration are the known pharmaceutical forms for such administration, for example sterile suspensions or sterile solutions in a suitable solvent.

Compositions for topical administration may comprise a matrix in which the pharmacologically active compounds of the present invention are dispersed so that the compounds are held in contact with the skin in order to administer the compounds transdermally. A suitable transdermal composition may be prepared by mixing the pharmaceutically active compound with a topical vehicle, such as a mineral oil, petrolatum and/or a wax, for example paraffin wax or beeswax, together with a potential transdermal accelerant such as dimethyl sulphoxide or propylene glycol. Alternatively the active compounds may be dispersed in a pharmaceutically acceptable cream or ointment base. The amount of active compound contained in a topical formulation should be such that a therapeutically effective amount of the compound is delivered during the period of time for which the topical formulation is intended to be on the skin.

The compounds of the present invention may also be administered by continuous infusion either from an external source, for example by intravenous infusion or from a source of the compound placed within the body. Internal sources include implanted reservoirs containing the compound to be infused which is continuously released for example by osmosis and implants which may be (a) liquid such as a suspension or solution in a pharmaceutically acceptable oil of the compound to be infused for example in the form of a very sparingly water-soluble derivative such as a dodecanoate salt or ester or (b) solid in the form of an implanted support, for example of a synthetic resin or waxy material, for the compound to be infused. The support may be a single body containing all the compound or a series of several bodies each containing part of the compound to be delivered. The amount of active compound present in an internal source should be such that a therapeutically effective amount of the compound is delivered over a long period of time.

In some formulations it may be beneficial to use the compounds of the present invention in the form of particles of very small size, for example as obtained by fluid energy milling.

In the compositions of the present invention the active compound may, if desired, be associated with other compatible pharmacologically active ingredients.

The present invention also comprises the use of a compound of formula I as a medicament.

The pharmaceutical compositions containing a therapeutically effective amount of a compound of formula I or a salt thereof may be used to treat depression, anxiety, psychoses (for example schizophrenia), tardive dyskinesia, Parkinson's disease, obesity, hypertension, Tourette's syndrome, sexual dysfunction, drug addiction, drug abuse, cognitive disorders, Alzheimers disease, senile dementia, obsessive-compulsive behaviour, panic attacks, social phobias, eating disorders, anorexia, cardiovascular and cerebrovascular disorders, non-insulin dependent diabetes mellitus, hyperglycaemia, constipation, arrhythmia, disorders of the neuroendocrine system, stress, prostatic hypertrophy, and spasticity in human beings. Whilst the precise amount of active compound administered in such treatment will depend on a number of factors, for example the age of the patient, the severity of the condition and the past medical history and always lies within the sound discretion of the administering physician, the amount of active compound administered per day is in the range 1 to 1000 mg preferably 5 to 500 mg given in single or divided doses at one or more times during the day.

A further aspect of the present invention provides the use of a compound of formula I in the manufacture of a medicament for treating depression, anxiety, psychoses (for example schizophrenia), tardive dyskinesia, Parkinson's disease, obesity, hypertension, Tourette's syndrome, sexual dysfunction, drug addiction, drug abuse, cognitive disorders, Alzheimer's disease, senile dementia, obsessive-compulsive behaviour, panic attacks, social phobias, eating disorders and anorexia, cardiovascular and cerebrovascular disorders, non-insulin dependent diabetes mellitus, hyperglycaemia, constipation, arrhythmia, disorders of the neuroendocrine system, stress, prostatic hypertrophy, or spasticity in human beings.

The present invention also provides a method of treating depression, anxiety, psychoses (for example schizophrenia), tardive dyskinesia, Parkinson's disease, obesity, hypertension, Tourette's syndrome, sexual dysfunction, drug addiction, drug abuse, cognitive disorders, Alzheimer's disease, senile dementia, obsessive-compulsive behaviour, panic attacks, social phobias, eating disorders and anorexia, cardiovascular and cerebrovascular disorders, non-insulin dependent diabetes mellitus, hyperglycaemia, constipation, arrhythmia, disorders of the neuroendocrine system, stress, prostatic hypertrophy, or spasticity in human beings which comprises the administration of a therapeutically effective amount of a compound of formula I to a patient in need thereof.

Processes for the preparation of compounds of formula I will now be described. These processes form a further aspect of the present invention. The processes are preferably carried out at atmospheric pressure. The substituents are as defined for formula I above unless otherwise stated.

Compounds of formula I in which Q is a group of formula IIa in which $R_5$ is H, and V is $(CH_2)_{n+1}$ wherein n is 0,1 or 2, and R" and R'" are other than formyl may be prepared by the reaction of a compound of formula III

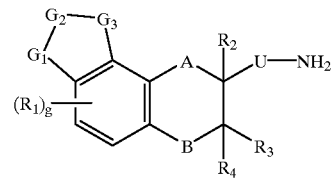

III with a compound of formula IV

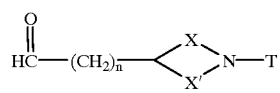

IV followed by reaction of the intermediate imine with a reducing agent, for example sodium borohydride.

Compounds of formula I in which Q is a group of formula IIa in which $R_5$ is H, and V is $(CH_2)_{n+1}$ wherein n is 0,1 or 2 may be prepared by the reaction of a compound of formula III with a compound of formula V

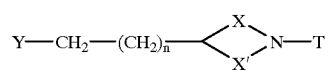

V in which Y is a leaving group, for example toluene-4-sulphonyloxy, optionally in the presence of a suitable solvent, optionally in the presence of a base, for example potassium carbonate.

Compounds of formula I in which Q is a group of formula IIa in which $R_5$ is H, and V is $(CH_2)_{n+1}$ wherein n is 0,1 or 2 may be prepared by reaction of a compound of formula VI

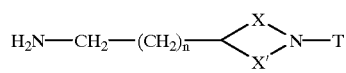

VI with a compound of formula VII

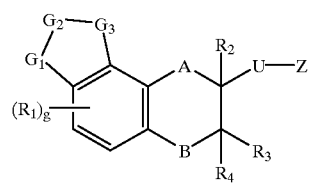

VII in which Z is a leaving group, for example toluene-4-sulphonyloxy, optionally in the presence of a suitable solvent, optionally in the presence of a base, for example potassium carbonate.

Compounds of formula I in which U is methylene and Q is a group of formula IIa in which $R_5$ is H, and V is $(CH_2)_{n+1}$ wherein n is 0, 1 or 2, and R" and R'" are other than formyl may be prepared by reaction of a compound of formula VIII

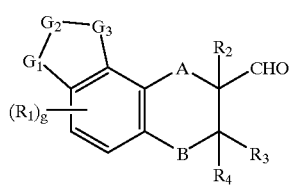

VIII with a compound of formula VI, followed by reduction of the intermediate imine with a suitable reducing agent, for example sodium borohydride.

Compounds of formula I in which $R_5$ is an alkyl group and R" and R'" are other than formyl may be prepared by alkylation of a compound of formula I in which $R_5$ is H with for example formaldehyde and formic acid, or an aldehyde and a reducing agent such as sodium cyanoborohydride.

Compounds of formula IIII may be prepared from compounds of formula IX

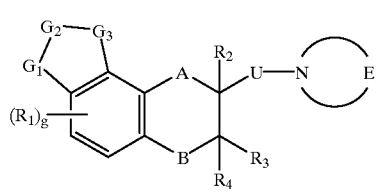

IX in which E together with the nitrogen atom to which it is attached is a suitable cyclic imide, for example a phthalimide, by acid or base catalysed hydrolysis or by cleavage with a reagent, for example hydrazine hydrate.

Compounds of formula IX in which E together with the nitrogen atom to which it is attached is a phthalimide may be prepared by reaction of a compound of formula VII in which Z is a leaving group, for example toluene-4-sulphonyloxy, with potassium phthalimide.

Compounds of formula IV may be prepared by reaction of a compound of formula X

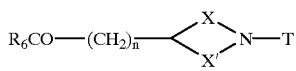

X in which $R_6$ is an alkoxy group containing 1 to 4 carbon atoms, with a reducing agent, for example sodium bis (2-methoxyethoxy)aluminium hydride in a solvent, for example toluene.

Compounds of formula X may be prepared by reaction of a compound of formula XI

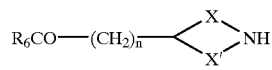

XI with an acylating agent of formula $X_2$-CO.HET in which $X_2$ is a leaving group, for example halo, alkoxy, hydroxy or alkoxycarbonyloxy, in the presence of a base, for example triethylamine, or an amide bond forming agent, for example carbonyl diimidazole, in a suitable solvent such as dichloromethane.

Compounds of formula IV may also be prepared by oxidation of a compound of formula XII

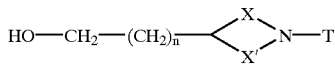

XII with a suitable oxidising agent, for example oxalyl chloride/dimethyl sulphoxide.

Compounds of formula V in which Y is toluene-4-sulphonyloxy may be prepared by reaction of a compound of formula XII with a tosylating agent, for example toluene-4-sulphonyl chloride.

Compounds of formula XII may be prepared by reaction of a compound of formula XIII

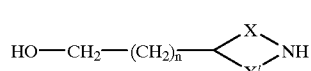

XIII with an acylating agent of formula $X_2$-CO.HET in which $X_2$ is a leaving group, for example halo, alkoxy, hydroxy or alkoxycarbonyloxy, in the presence of a base, for example triethylamine, or an amide bond forming agent, for example carbonyl diimidazole, in a suitable solvent such as dichloromethane.

Compounds of formula XIII may be prepared by reduction of a compound of formula XI, in which $R_6$ is an alkoxy group containing 1 to 4 carbon atoms, with a reducing agent, for example lithium aluminium hydride.

Compounds of formula VI may be prepared by reaction of a compound of formula XIV

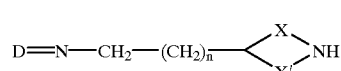

XIV in which D is a protecting group, for example 5-bromo-2-hydroxybenzylidene, with an acylating agent of formula $X_2$-CO.HET in which $X_2$ is a leaving group, for example halo, alkoxy, hydroxy or alkoxycarbonyloxy, in the presence of a base, for example triethylamine, or an amide bond forming agent, for example carbonyl diimidazole, in a suitable solvent such as dichloromethane, followed by removal of the protecting group, for example by acid-catalysed hydrolysis.

Compounds of formula XIV may be prepared by reaction of a compound of formula XV

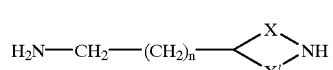

XV with a protecting reagent, for example 5-bromo-2-hydroxybenzaldehyde.

Compounds of formula XV may be prepared by reduction of a compound of formula XI in which $R_6$ is $NH_2$ with a reducing agent, for example lithium aluminium hydride.

Compounds of formula VII in which Z is toluene-4-sulphonyloxy may be prepared by reaction of a compound of formula XVI

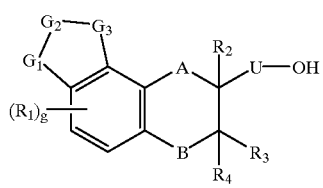

XVI with a tosylating agent, for example toluene-4-sulphonyl chloride, optionally in the presence of a base, for example pyridine.

Compounds of formula XVI in which A and B are both —O—, $R_2$, $R_3$ and $R_4$ are all H, and U is methylene may be prepared by reaction of a compound of formula XVII

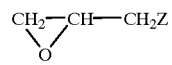

XVII in which Z is a leaving group, for example chloro or toluene-4-sulphonyloxy, with a compound of formula XVIII

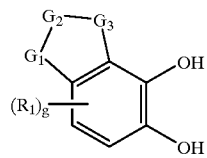

XVIII in a suitable solvent, for example water or dimethylformamide in the presence of a base, for example sodium hydroxide. When an enantiomerically pure form of a compound of formula XVII, for example (R)-glycidyl-4-toluenesulphonate, is used, the single (S)-enantiomer of a compound of formula XVI can be prepared.

Compounds of formula XVI in which A and B are both —O—, U is methylene, and $R_2$, $R_3$ and $R_4$ are all H, may also be prepared by cyclisation of a compound of formula XIX

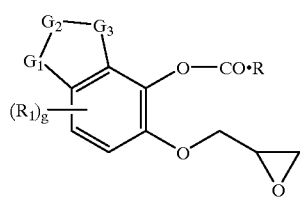

XIX in which R is H or an alkyl group containing 1 to 4 carbon atoms, using a base, for example potassium carbonate.

Compounds of formula XIX may be prepared by oxidation of compounds of formula XX

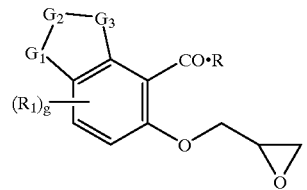

XX in which R is H or an alkyl group containing 1 to 4 carbon atoms, with a peroxyacid, for example 3-chloroperoxybenzoic acid.

Compounds of formula XX may be prepared by alkylating compounds of formula XXI

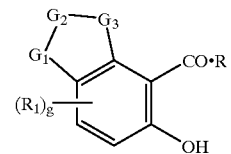

XXI in which R is H or an alkyl group containing 1 to 4 carbon atoms, with compounds of formula XVII, in which Z is a leaving group, for example chloro or toluene-4-sulphonyloxy, in a suitable solvent, for example dimethylformamide, in the presence of a base, for example potassium carbonate.

Compounds of formula XVI in which A and U are methylene, B is —O—, $R_2$ is H and R" and R'" are H or cyano, may be prepared by reduction of a compound of formula XXII

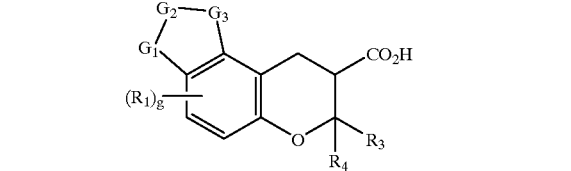

XXII with a reducing agent, for example borane-dimethyl sulphide complex.

Compounds of formula XXII may be prepared by reduction of a compound of formula XXIII

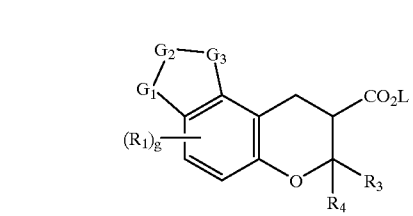

XXIII in which L is H with a reducing agent, for example hydrogen in the presence of a palladium-on-carbon catalyst.

Compounds of formula XXIII in which L is H may be prepared by acid or base-catalysed hydrolysis of a compound of formula XXIII in which L is an alkyl group containing 1 to 6 carbon atoms.

Compounds of formula XXIII in which L is an alkyl group may be prepared by reaction of a compound of formula XXI in which R is H with a compound of formula

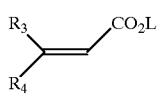
XXIV in which L is an alkyl group containing 1 to 6 carbon atoms, in the presence of a base, for example 1,4-diazabicyclo[2.2.2]octane (DABCO).

Compounds of formula VIII may be prepared by oxidation of a compound of formula XVI in which U is methylene with a suitable oxidising agent, for example pyridinium chlorochromate or by reduction of a compound of formula XXV

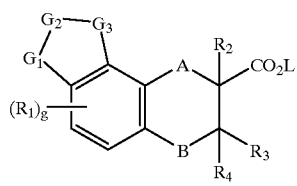
XXV with a suitable reducing agent, for example sodium bis(2-methoxyethoxy)aluminium hydride in a solvent, for example toluene.

Compounds of formula XXV in which A and B are both —O— may be prepared by reaction of a compound of formula XXVI

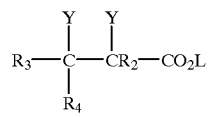
XXVI in which Y is a leaving group, for example bromo, and L is an alkyl group containing 1 to 6 carbon atoms with a compound of formula XVIII, in the presence of a base, for example potassium carbonate.

Compounds of formula XXV in which A is methylene, B is —O—, $R_2$ is H and L is an alkyl group containing 1 to 6 carbon atoms may be prepared by reduction of a compound of formula XXIII in which L is an alkyl group containing 1 to 6 carbon atoms, with a suitable reducing agent, for example hydrogen in the presence of a palladium-on-carbon catalyst.

Compounds of formula I in which Q is a group of formula IIa may be prepared by reaction of compound of formula XXVII

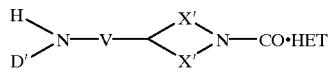
XXVII in which D' is H, with a compound of formula VII in which Z is a leaving group, for example toluene-4-sulphonyloxy, optionally in the presence of a base, for example potassium carbonate, and optionally in a solvent, for example acetonitrile.

Compounds of formula XXVII in which D' is H may be prepared by deprotection of a compound of formula XXVII in which D' is a protecting group, for example tert-butoxycarbonyl, for example by acid hydrolysis in the presence of an acid, for example trifluoroacetic acid.

Compounds of formula XXVII in which D' is a protecting group may be prepared by reaction of a compound of formula XXVIII

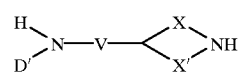
XXVIII in which D' is a protecting group, for example tert-butoxycarbonyl, with a compound of formula $X_2$-CO.HET in which $X_2$ is a leaving group, for example halo, alkoxy, hydroxy or alkoxycarbonyloxy, in the presence of a base, for example triethylamine, or an amide bond forming agent, for example carbonyl diimidazole, in a suitable solvent such as dichloromethane.

Compounds of formula XXVII in which D' is a protecting group and HET is of the formula XXIX

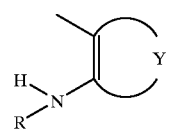
XXIX in which Y completes a heteroaromatic ring and R is H or alkyl, may be prepared by reaction of a compound of formula XXVIII with a compound of formula XXX

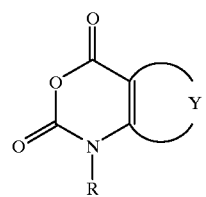
XXX in which Y completes a heteroaromatic ring and R is H or an alkyl group, in a solvent, for example 1,2-dimethoxyethane.

Compounds of formula I in which Q is a group of formula IIb may be prepared by reaction of a compound of formula XXXI

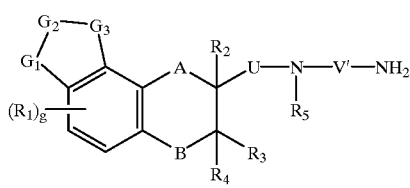
XXXI with an acylating agent of formula $X_2$-CO.HET in which $X_2$ is a leaving group, for example halo, alkoxy, hydroxy or alkoxycarbonyloxy, in the presence of a base, for example triethylamine, or an amide bond forming agent, for example carbonyl diimidazole, in a suitable solvent such as dichloromethane.

Compounds of formula I in which Q is a group of formula IIb may be prepared by reaction of a compound of formula VII in which Z is a leaving group, for example toluene-4-sulphonyloxy, with a compound of formula XXXII

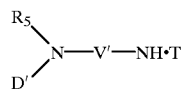

XXXII in which D' is H, optionally in the presence of a base, for example potassium carbonate, and optionally in a solvent, for example acetonitrile.

Compounds of formula XXXI may be prepared from a compound of formula XXXIII

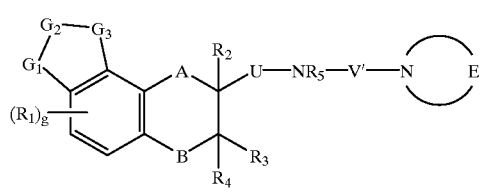

XXXIII in which E together with the nitrogen atom to which it is attached is a cyclic imide, for example a phthalimide, by acid or base catalysed hydrolysis or by cleavage with a reagent, for example hydrazine hydrate.

Compounds of formula XXXIII in which E together with the nitrogen atom to which it is attached is a phthalimide and $R_5$ is H may be prepared by reaction of a compound of formula III with a haloalkyl phthalimide, for example N-(3-bromopropyl)phthalimide, optionally in the presence of a base, for example potassium carbonate.

Compounds of formula XXXII in which D' is H may be prepared by deprotection of a compound of formula XXXII in which D' is a protecting group, for example tert-butoxycarbonyl, for example by acid hydrolysis in the presence of an acid, for example trifluoroacetic acid.

Compounds of formula XXXII in which D' is a protecting group may be prepared by reaction of a compound of formula XXXIV

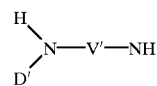

XXXIV in which D' is a protecting group, for example tert-butoxycarbonyl, with a compound of formula $X_2$-CO.HET in which $X_2$ is a leaving group, for example halo, alkoxy, hydroxy or alkoxycarbonyloxy, in the presence of a base, for example triethylamine, or an amide bond forming agent, for example carbonyl diimidazole, in a suitable solvent such as dichloromethane.

Compounds of formula XXXII in which D' is a protecting group and HET is of the formula XXIX in which Y completes a heteroaromatic ring and R is H or alkyl, may be prepared by reaction of a compound of formula XXXIV with a compound of formula XXX in which Y completes a heteroaromatic ring and R is H or an alkyl group, in a solvent, for example 1,2-dimethoxyethane.

Compounds of formula I in which Q is a group of formula IIc may be prepared by reaction of a compound of formula XXXV

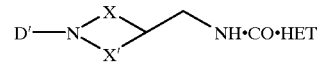

XXXV in which D' is H, with a compound of formula VII in which Z is a leaving group, for example toluene-4-sulphonyloxy, optionally in the presence of a base, for example potassium carbonate, and optionally in a solvent, for example acetonitrile, at a temperature in the range 0–2000° C., preferably in the range 20–150° C.

Compounds of formula XXXV in which D' is H may be prepared by deprotection of a compound of formula XXXV in which D' is a protecting group, for example tert-butoxycarbonyl, for example by acid hydrolysis in the presence of an acid, for example trifluoroacetic acid.

Compounds of formula XXXV in which D' is a protecting group may be prepared by reaction of a compound of formula XXXVI

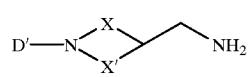

XXXVI in which D' is a protecting group, for example tedt-butoxycarbonyl, with a compound of formula $X_2$-CO.HET in which $X_2$ is a leaving group, for example halo, alkoxy, hydroxy or alkoxycarbonyloxy, in the presence of a base, for example triethylamine, or an amide bond forming agent, for example carbonyl diimidazole, in a suitable solvent such as dichloromethane.

Compounds of formula XXXV in which D' is a protecting group and HET is of the formula XXIX in which Y completes a heteroaromatic ring and R is H or alkyl, may be prepared by reaction of a compound of formula XXXVI with a compound of formula XXX in which Y completes a heteroaromatic ring and R is H or alkyl, in a solvent for example 1,2-dimethoxyethane.

Compounds of formula I in which Q is a group of formula IIc and HET is of the formula XXIX may be prepared by reaction of a compound of formula XXXVII

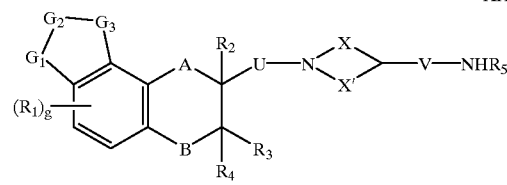

XXXVII with a compound of formula XXX, for example pyrido[2,3d][1,3]oxazine-2,4(1H)-dione optionally in the presence of a solvent, for example 1,2-dimethoxyethane.

Compounds of formula XXXVII in which $R_5$ is H may be prepared from compounds of formula XXXVIII

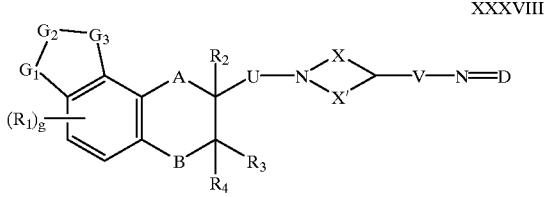

XXXVIII in which D is a protecting group, for example 5-bromo-2-hydroxybenzylidene, by acid or base catalysed hydrolysis.

Compounds of formula XXXVIII may be prepared by reaction of a compound of formula XXXIX

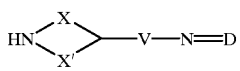

XXXIX in which D is a protecting group, for example 5-bromo-2-hydroxybenzylidene, with a compound of formula VII, optionally in the presence of a base, for example triethylamine.

Compounds of formula XXXIX may be prepared by reaction of a compound of formula XL

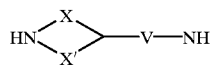

XL with a protecting reagent, for example 5-bromo-2-hydroxybenzaldehyde.

Compounds of formula VII in which $G_1$—$G_2$—$G_3$ are —NH—CH=CH— are known (J.Med.Chem.,1992,35, pg 3058). Compounds of formula VII in which $G_1$—$G_2$—$G_3$ are other than —NH—CH=CH— may be prepared by methods analogous to that disclosed in the above reference by selecting the appropriate starting materials.

Compounds of formula I in which HET is 2-amino-3-pyridyl may be prepared by the reaction of the corresponding compound of formula I in which HET is 2-chloro-3-pyridyl with aqueous ammonia solution.

The ability of compounds of formula I to interact with 5-hydroxytryptamine (5-HT) receptors has been demonstrated by the following test which determines the ability of the compounds to inhibit tritiated ligand binding to 5-HT receptors in vitro and in particular to $5\text{-HT}_{1A}$ receptors.

Hippocampal tissue from the brains of male Charles River CD rats weighing between 150–250 g were homogenised in ice-cold 50 mM Tris-HCl buffer (pH 7.7) when measured at 25° C., 1:40 w/v) and centrifuged at 30,000 g at 4° C. for 10 minutes. The pellet was rehomogenised in the same buffer, incubated at 37° C. for 10 minutes and centrifuged at 30,000 g at 4° C. for 10 minutes. The final pellet was resuspended in 50 mM Tris-HCl buffer (pH 7.7) containing 4 mM $CaCl_2$, 0.1% L-ascorbic acid and 10 μM pargyline hydrochloride (equivalent to 6.25 mg wet weight of tissue/ml) and used immediately in the binding assay. Aliquots (400 μl; equivalent to 2.5 mg wet weight of tissue/tube) of this suspension were added to tubes containing the ligand (50 μl; 2 nM) and distilled water (50 μl; total binding) or 5-HT (50 μl; 10 μM; non-specific binding) or test compound (50 μl; at a single concentration of $10^{-6}$ M or at 10 concentrations ranging from $10^{-11}$–$10^{-3}$ M). The ligand was [$^3$H]8-hydroxy-2-(dipropylamino)tetralin ([$^3$H]8-OH-DPAT) and the mixture was incubated at 25° C. for 30 minutes before the incubation was terminated by rapid filtration.

The filters were washed with ice-cold Tris-HCl buffer and dried. The filters were punched out into vials, scintillation fluid added and radioactivity determined by liquid scintillation counting. The percentage displacement of specific binding of the tritiated ligand was calculated for the single concentration ($10^{-6}$ M) of test compound. Displacement curves were then produced for those compounds which displaced ≧50% of specific binding of the tritiated ligand at $10^{-6}$ M using a range of concentrations of the compound. The concentration which gave 50% inhibition of specific binding ($IC_{50}$) was obtained from the curve. The inhibition coefficient Ki was then calculated using the formula $$K_i = \frac{IC50}{1 + ([ligand]/K_D)}$$

in which [ligand] is the concentration of the tritiated ligand used and $K_D$ is the equilibrium dissociation constant for the ligand.

The ability of compounds of formula I to interact with adrenoceptor binding sites has been demonstrated by the following test which determines the ability of the compounds to inhibit tritiated ligand binding to adrenoceptors in vitro and in particular $\alpha_1$-adrenoceptors.

Whole cortical tissue from the brains of male Charles River CD rats weighing between 150–250 g were homogenised in ice-cold 50 mM Tris-HCl, pH 7.6 (at 25° C.; 1:40 w/v) and centrifuged at 1000 g at 4° C. for 10 minutes. The supernatant was centrifuged at 30,000 g at 4° C. for 10 minutes. The pellet was rehomogenised in 50 mM Tris-HCl, pH 7.6 (1:40 w/v) and centrifuged at 30,000 g at 4° C. for 10 minutes. The final pellet was resuspended in 50 mM Tris-HCl, pH 7.6 (equivalent to 12.5 mg wet weight of tissue/ml) and used immediately in the binding assay. Aliquots (400 μl; equivalent to 5 mg wet weight of tissue/tube) of this suspension were added to tubes containing the ligand (50 μl; 0.1 nM) and distilled water (50 μl; total binding) or phentolamine (50 μl; 5 μM; non-specific binding) or test compound (50 μl; at a single concentration of $10^{-6}$M or at 10 concentrations ranging from $10^{-11}$–$10^{-4}$M). The ligand was [7-methoxy-$^3$H]prazosin and the mixture was incubated at 30° C. for 30 minutes before the incubation was terminated by rapid filtration.

The filters were washed with ice-cold Tris-HCl buffer and dried. The filters were punched out into vials, scintillation fluid added and radioactivity determined by liquid scintillation counting. The percentage displacement of specific binding of the tritiated ligand was calculated for the single concentration ($10^{-6}$ M) of test compound. Displacement curves were then produced for those compounds which displaced ≧50% of specific binding of the tritiated ligand at $10^{-6}$ M using a range of concentrations of the compound. The concentration which gave 50% inhibition of specific binding ($IC_{50}$) was obtained from the curve. The inhibition coefficient Ki was then calculated using the formula $$K_i = \frac{IC50}{1 + ([ligand]/K_D)}$$

in which [ligand] is the concentration of the tritiated ligand used and $K_D$ is the equilibrium dissociation constant for the ligand.

The ability of compounds of formula I to interact with dopamine receptors has been demonstrated by the following test which determines the ability of the compounds to inhibit tritiated ligand binding to dopamine receptors in vitro and in particular to the $D_2$-like dopamine receptors.

Striatal tissue from the brains of male Charles River CD rats weighing between 140–250 g were homogenised in ice-cold 50 mM Tris-HCl buffer (pH 7.7 when measured at 25° C.) and centrifuged at 40,000 g for 10 minutes. The pellet was resuspended in Tris salts buffer (50 mM Tris-HCl buffer containing 120 mM NaCl, 5 mM KCl, 2 mM $CaCl_2$ and 1 mM $MgCl_2$ with the addition of 6 mM ascorbic acid; pH 7.7 when measured at 25° C.), and again centrifuged at 40,000 g for 10 minutes. The final pellet was stored at −80° C. Before each test the pellet was resuspended in Tris salts buffer (equivalent to 2 mg wet weight of tissue/ml). Aliquots (720 µl; equivalent to 1.44 mg wet weight of tissue/tube) of this suspension were then added to tubes containing the ligand (40 µl; 1 nM) and Tris salts buffer (40 µl; total binding) or spiroperidol (40 µl; 10 nM; non-specific binding) or test compound (40 µl; at a single concentration of $10^{-6}$M or at 6 concentrations ranging from $10^{-11}$–$10^{-4}$M). The ligand was tritiated (S)-suipiride and the mixture was incubated at 4° C. for 40 minutes before the incubation was terminated by rapid filtration.

The filters were washed with ice-cold Tris-HCl buffer and dried. The filters were punched out in to vials, scintillation fluid added and were left for about 20 hours before being counted by scintillation spectrophotometry. The percentage displacement of specific binding of the tritiated ligand was calculated for the single concentration ($10^{-6}$M) of test compound. Displacement curves were then produced over a range of concentrations for those compounds which displaced ≧50% of specific binding of the tritiated ligand at $10^{-6}$M. The concentration which gave a 50% inhibition of specific binding (IC50) was obtained from the curve. The inhibition coefficient Ki was then calculated using the formula $$K_i = \frac{IC50}{1 + ([ligand]/K_D)}$$

in which [ligand] is the concentration of the tritiated ligand used and $K_D$ is the equilibrium dissociation constant for the ligand.

The $K_i$ values obtained in the above tests for 5-$HT_{1A}$, $\alpha_1$, and $D_2$-like binding for each of the final products of Examples 1 and 2 hereinafter are given in Table I below.

TABLE 1

| Example Number | Ki (nM) value for | | |
| --- | --- | --- | --- |
| | 5-$HT_{1A}$ | $D_2$-like | $\alpha_1$ |
| 1 | 3.1 | 7.6 | 12.4 |
| 2 | 99% | 122% | 93% |

The % figures in Table 1 are for % displacement at $10^{-6}$M.

The invention is illustrated by the following Examples which are given by way of example only. The final product of Examples 1 and 2 were characterised by one or more of the following procedures: gas-liquid chromatography; high performance liquid chromatography; elemental analysis, nuclear magnetic resonance spectroscopy and infrared spectroscopy.

EXAMPLE 1

Potassium carbonate (0.89 g) was added under nitrogen to a stirred solution of ethyl 4-formyl-5-hydroxyindole-2-carboxylate (1.50 g) in dry dimethylformamide (40 ml). A solution of (R)-glycidyl 4-toluenesulphonate (1.47 g) in dry dimethylformamide (30 ml) was then added and the mixture stirred at ambient temperature for 10 minutes, then at 60° C. for 3 hours. The mixture was poured into water (400 ml) and extracted with ethyl acetate (3×200 ml). The combined extracts were washed with brine (6×200 ml), dried over magnesium sulphate and the solvent evaporated under reduced pressure. The brown solid residue was purified by flash column chromatography on silica eluting with a 1:1 mixture of petroleum ether (b.p. 40–60° C.) and ethyl acetate to give ethyl (R)-5-(2,3-epoxypropoxy)-4-formylindole-2-carboxylate (1.07 g) as an off-white solid; m.p. 152–154° C.

A stirred solution of ethyl (R)-5-(2,3-epoxypropoxy)-4-formylindole-2-carboxylate (1.95 g; prepared by the method described above) in dichloromethane (40 ml) was cooled to 0° C. 3-Chloroperoxybenzoic acid (85%; 1.75 g) was then added in one portion followed by a solution of trifluoroacetic acid (0.77 g) in dichloromethane (10 ml), in portions. The mixture was stirred at 0° C. for 10 minutes and then at ambient temperature for 1 hour. The reaction mixture was diluted with dichloromethane (300 ml), washed successively with saturated aqueous sodium bisulphite solution (100 ml), saturated aqueous sodium bicarbonate solution (3×150 ml), dried over sodium sulphate and the solvent evaporated. The solid residue was purified by flash chromatography on silica eluting with a 1:1 mixture of petroleum ether (b.p. 40–60° C.) and ethyl acetate to give ethyl (R)-5-(2,3-epoxypropoxy)-4-formyloxyindole-2-carboxylate (1.55 g) as a pale yellow crystalline solid; m.p. 123–125° C.

Saturated aqueous potassium carbonate solution (200 ml) was added to a stirred solution of ethyl (R)-5-(2,3-epoxypropoxy)-4-formyloxyindole-2-carboxylate (22.0 g; prepared in a similar manner to that described above) in tetrahydrofuran (250 ml) and the mixture was stirred at room temperature for 72 hours. The mixture was poured into water (1000 ml) and extracted with ethyl acetate (4×400 ml). The combined extracts were dried over sodium sulphate and the solvent evaporated under reduced pressure to give ethyl (S)-2,3-dihydro-2-(hydroxymethyl)-7H-1,4-dioxino[2,3-e]indole-8-carboxylate (17.65 g) as a pale purple solid; m.p. 152–153° C.

A solution of lithium hydroxide monohydrate (0.94 g) in water (25 ml) was added to a stirred solution of the product from the previous reaction (2.95 g) in methanol (50 ml) under nitrogen and the resulting solution stirred at 60° C. for 1 hour. The methanol was then removed by evaporation and water (80 ml) added. Hydrochloric acid (2M) was then added until the mixture was pH 2, and the resulting precipitate collected by filtration, washed with water and dried to give (S)-2,3-dihydro-2-(hydroxymethyl)-7H-1,4-dioxino[2,3-e]indole-8-carboxylic acid (2.61 g) as a solid; m.p. 216–217° C.

A flask containing the product from the previous reaction (2.60 g) was plunged into a pre-heated isomantle at 250° C. under nitrogen and the material heated at 250–60° C. for 30 minutes. The residue was cooled to ambient temperature, pre-absorbed from a methanol solution onto silica and purified by flash column chromatograhy on silica eluting with 1:1 mixture of petroleum ether (b.p. 40–60° C.) and ethyl acetate to give (S)-2,3-dihydro-7H-1,4-dioxino-[2,3-e]indol-2-ylmethanol (0.69 g) as a colouriess syrup.

A solution of (S)-2,3-dihydro-7H-1,4-dioxino[2,3-e]indol-2-ylmethanol (0.75 g; prepared by the method described above) in dichloromethane (50 ml) was stirred with cooling in an ice bath. 4-(Dimethylamino)pyridine (0.59 g) and 4-toluenesulphonyl chloride (0.84 g) were then added and the solution stirred at ambient temperature overnight. The mixture was diluted with dichloromethane (200 ml), washed sucessively with water (50 ml), saturated aqueous copper(II) sulphate solution (2×50 ml) and water (50 ml), then dried over sodium sulphate and the solvent evaporated to give (S)-2,3-dihydro-7H-1,4-dioxino[2,3-e]indol-2-ylmethyl 4-toluenesulphonate (1.04 g) as a pale brown oil which solidified on standing.

Trifluoroacetic acid (10 ml) was added dropwise to a stirred solution of 2-amino-N-(1-tert-butoxycarbonylpiperid-4-yl)methylpyridine-3-carboxamide (0.40 g) in dichloromethane (15 ml) and the mixture stirred at room temperature for 2 hours. The solvent was evaporated under reduced pressure and the oily residue dissolved in dry acetonitrile (20 ml). Potassium carbonate (5.0 g) and a solution of the product from the previous reaction (0.41 g) in dry acetonitrile (10 ml) were then added and the mixture heated under reflux with stirring for 24 hours. The cooled reaction mixture was filtered and the solvent removed evaporated under reduced pressure. The residue was dissolved in dichloromethane (50 ml), washed with water (3×50 ml), dried over magnesium sulphate and the solvent evaporated. The residue was purified by flash chromatograhy on silica eluting with a 20:1 mixture of dichloromethane and methanol to give (S)-2-amino-N-{[1-(2,3-dihydro-7H- 1,4-dioxino[2,3-e]indol-2-ylmethyl)-4-piperidyl]methyl}pyridine-3-carboxamide (0.27 g); m.p. 104–106° C., [ ]$_D$-36.8° (c=0.367 in MeOH).

EXAMPLE 2

Trifluoroacetic acid (5 ml) was added to stirred solution of N-(1-tent-butoxy-carbonylpiperid-4-yl)methylpyridine-2-carboxamide (1.00 g) in dichloromethane (20 ml) and the mixture stirred at room temperature for 2 hours. The solvent was evaporated under reduced pressure and the residue dissolved in dry acetonitrile (30 ml). Potassium carbonate (5.0 g) and a solution of (S)-2,3-dihydro-7H-1,4-dioxino[2,3-e]indol-2-ylmethyl 4-toluenesulphonate (1.00 g) in dry acetonitrile (15 ml) were then added and the mixture heated under reflux with stirring for 24 hours. The cooled mixture was filtered and the solvent removed. The residue was dissolved in dichloromethane (300 ml), washed with water (100 ml), dried over sodium sulphate and the solvent evaporated. The residual pale brown oil was purified by flash column chromatography on silica eluting with a 9:1 mixture of ethyl acetate and methanol to give the product free base as a pale-yellow oil. A solution of the product in hot ethanol (5 ml) was treated with a hot solution of fumaric acid (0.15 g) in ethanol (10 ml) and the solution then evaporated under reduced pressure. The resulting solid was triturated with diethyl ether to give (S)-N-{[1-(2,3-dihydro-7H-1,4-dioxino[2,3-e]indol-2-ylmethyl)-4-piperidyl]methyl}pyridine-2-carboxamide 1.3 fumarate, 0.25 diethyl ether, 1.0 hydrate (588 mg); m.p.122–5° C., [ ]$_D$-23.30(c=0.391 in EtOH).

EXAMPLES 3–27

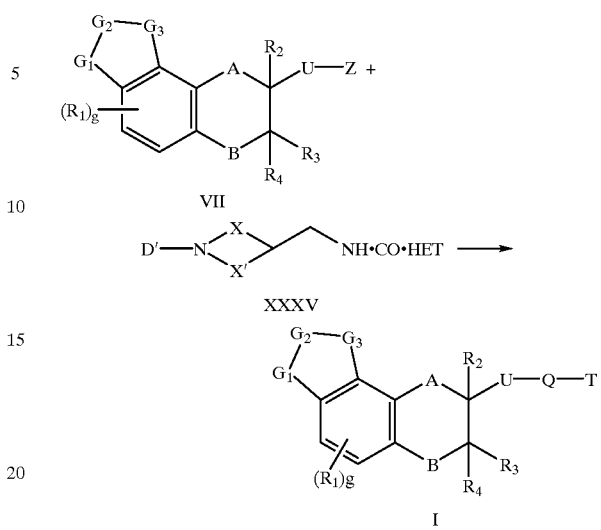

The following compounds are prepared in a similar manner to that described in Example 1, by selection of the appropriate compounds of formula VII and XXXV (D' in XXXV being H):

3 Ethyl 2,3-dihydro-2-({4-[(2-pyridinecarboxamido)methyl]piperdino}methyl)-7H-1,4-dioxino[2,3-e]indole-8-carboxylate
4 Ethyl 2,3-dihydro-2-({4-[(3-pyridinecarboxamido)methyl]piperidino}methyl)-7H-1,4-dioxino[2,3-e]indole-8-carboxylate
5 Ethyl 2-({4-[(2-amino-3-pyridinecarboxamido)methyl]piperidino}methyl)-2,3-dihydro-7H-1,4-dioxino[2,3-e]indole-8-carboxylate
6 2,3-Dihydro-2-({4-[(2-pyridinecarboxamido)methyl]piperidino}methyl)-7H-1,4-dioxino[2,3-e]indole-8-carboxamide
7 2,3-Dihydro-2-({4-[(3-pyridinecarboxamido)methyl]piperidino}methyl)-7H-1,4-dioxino[2,3-e]indole-8-carboxamide
8 2-({4-[(2-Amino-3-pyridinecarboxamido)methyl]piperidino}methyl)-2,3-dihydro-7H-1,4-dioxino[2,3-e]indole-8-carboxamide
9 2,3-Dihydro-N,N-dimethyl-2-({4-[(2-pyridinecarboxamido)methyl]piperidinol}-methyl)-7H-1,4-dioxino[2,3-e]indole-8-carboxamide
10 2,3-Dihydro-N,N-dimethyl-2-({4-[(3-pyridinecarboxamido)methyl]piperidino-}-methyl)-7H-1,4-dioxino[2,3-e]indole-8-carboxamide
11 2-({4-[(2-Amino-3-pyridinecarboxamido)methyl]piperidino}methyl)-2,3-dihydro-N,N-dimethyl-7H-1,4-dioxino[2,3-e]indole-8-carboxamide
12 N-{[1-(8-Acetyl-2,3-dihydro-7H-1,4-dioxino[2,3-e]indol-2-ylmethyl)-4-piperidyl]methyl}pyridine-2-carboxamide
13 N-{[1-(8-Acetyl-2,3-dihydro-7H-1,4-dioxino[2,3-e]indol-2-ylmethyl)-4-piperidyl]methyl}pyridine-3-carboxamide
14 N-{[1-(8-Acetyl-2,3-dihydro-7H-1,4-dioxino[2,3-e]indol-2-ylmethyl)-4-piperidyl]methyl}-2-aminopyridine-3-carboxamide
15 N-{[1-(8-Cyano-2,3-dihydro-7H-1,4-dioxino[2,3-e]indol-2-ylmethyl)-4-piperid]methyl}pyridine-2-carboxamide
16 N-{[1-(8-Cyano-2,3-dihydro-7H-1,4-dioxino[2,3-e]indol-2-ylmethyl)-4-piperidy]methyl}pyridine-3-carboxamide 17 2-Amino-N-{[1-(8-cyano-2,3-dihydro-7H-1,4-dioxino[2,3-e]indol-2-ylmethyl)-4-piperidyl]methyl}pyridine-3-carboxamide
18 N-{[1-(8-Formyl-2,3-dihydro-7H-1,4-dioxino[2,3-e]indol-2-ylmethyl)-4-piperidyl]methyl}pyridine-2-carboxamide
19 N-([1-(8-Formyl-2,3-dihydro-7H-1,4-dioxino[2,3-e]indol-2-ylmethyl)-4-piperidyl]methyl)pyridine-3-carboxamide
20 2-Amino-N-{[1-(8-formyl-2,3-dihydro-7H-1,4-dioxino[2,3-e]indol-2-ylmethyl)-4-piperidyl]methyl}pyridine-3-carboxamide
21 N-{[1-(2,3-Dihydro-7H-1,4-dioxino[2,3-e]indol-2-ylmethyl)-4-piperidyl]methyl}-2-methoxypyridine-3-carboxamide
22 N-{[1-(2,3-Dihydro-7H-1,4-dioxino[2,3-e]indazol-2-ylmethyl)-4-piperidyl]-methyl}pyridine-2-carboxamide
23 N-{[1-(2,3-Dihydro-7H-1,4-dioxino[2,3-e]indazol-2-ylmethyl)-4-piperidyl]-methyl}pyridine-3-carboxamide
24 2-Amino-N-{[1-(2,3-dihydro-7H-1,4-dioxino[2,3-e]indazol-2-ylmethyl)-4-piperidyl]methyl}pyridine-3-carboxamide
25 N-{[1-(2,3-Dihydro-7H-1,4-dioxino[2,3-e]benzimidazol-2-ylmethyl)-4-piperidyl]methyl}pyridine-2-carboxamide
26 N-{[1-(2,3-Dihydro-7H-1,4-dioxino[2,3-e]benzimidazol-2-ylmethyl)-4-piperidyl]methyl}pyridine-3-carboxamide
27 2-Amino-N-{[1-(2,3-dihydro-7H-1,4-dioxino[2,3-e]benzimidazol-2-yimethyl)-4-piperidyl]methyl}pyridine-3-carboxamide The free bases of these compounds can be converted into pharmaceutically acceptable salts by methods well known in the art.

EXAMPLES 28–30

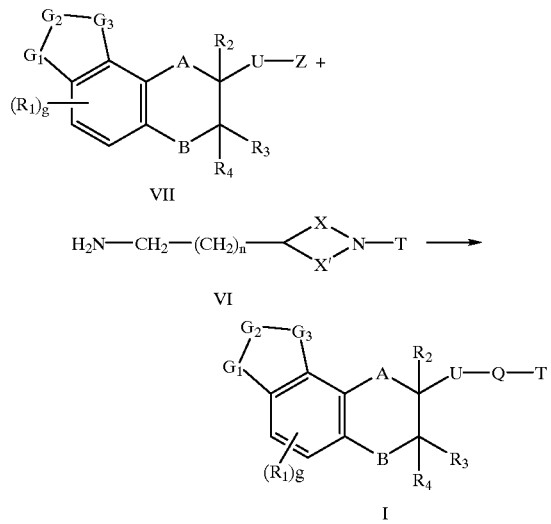

The following compounds are prepared in a similar manner to that described in Example 1, by selection of the appropriate compounds of formula VII and VI:
28 2,3-Dihydro-2-(N-{[1-(2-pyridylcarbonyl)-4-piperidyl]methyl}aminomethyl)-7H-1,4-dioxino[2,3-e]indole;
29 2,3-Dihydro-2-(N-{[1-(3-pyridylcarbonyl)-4-piperidyl]methyl}aminomethyl)-7H-1,4-dioxino[2,3-e]indole;
30 2-(N-{[1-(2-Chloro-3-pyridylcarbonyl)-4-piperidyl]methyl}aminomethyl)-2,3-dihydro-7H-1,4-dioxino[2,3-e]indole;

The free base of these compounds can be converted into a pharmaceutically acceptable salt by methods well known in the art.

EXAMPLE 31

The following compound may be prepared by amination of example 30 above:
31 2-(N-{[1-(2-Amino-3-pyridylcarbonyl)-4-piperidyl]methyl}aminomethyl)-2,3-dihydro-7H-1,4-dioxino[2,3-e]indole.

Preparation of Starting Materials

1) Compounds of Formula VII

These compounds, in which Z is toluene-4-sulphonyloxy, may be prepared by reaction of the appropriate compound of formula XVI in which A and B are both —O—, $R_2$, $R_3$ and $R_4$ are H, g is 0, U is methylene, and $G_1$—$G_2$—$G_3$ are as defined in Table 2.

TABLE 2

| $G_1$–$G_2$–$G_3$ | For Example No. |
|---|---|
| —NH—C(CO$_2$Et)=CH— | 3, 4, 5 |
| —NH—C(CONH$_2$)=CH— | 6, 7, 8 |
| —NH—C(CONMe$_2$)=CH— | 9, 10, 11 |
| —NH—C(COMe)=CH— | 12, 13, 14 |
| —NH—C(CN)=CH— | 15, 16, 17 |
| —NH—C(OHO)=CH— | 18, 19, 20 |
| —NH—CH=CH— | 21, 28, 29, 30 |
| —NH—N=CH— | 22, 23, 24 |
| —NH—CH=N— | 25, 26, 27 |

2) Compounds of Formula XXXV

 XXXV (D' is H)

Compounds of formula XXXV in which D' is H and X and X' are both ethylene may be prepared by acid hydrolysis, with, for example, trifluoroacetic acid, of the product of the reaction of the compound of formula XXXVI, in which D' is a protecting group, for example tert-butoxycarbonyl, and X and X' are both ethylene with the appropriate compound of formula $X_2$-CO.HET, as defined in Table 3.

TABLE 3

| $X_2$-CO.HET | For Example No. |
|---|---|
| ![pyridine-2-COOH] | 3, 6, 9, 12, 15, 18, 22, 25 |
| ![pyridine-3-COCl] | 4, 7, 10, 13, 16, 19, 23, 26 |
| ![MeO-pyridine-COCl] | 21 | b)

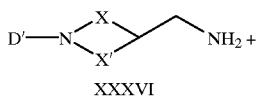 XXXVI

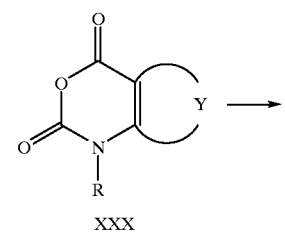 XXX

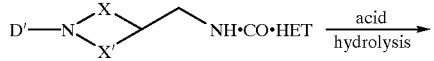 XXXV (D' is Protecting Group)

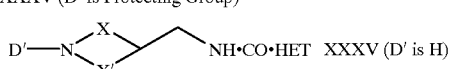 XXXV (D' is H)

Compounds of formula XXXV in which D' is H and X and X' are both ethylene may be prepared by reaction of a compound of formula XXXVI, in which D' is a protecting group, for example tert-butoxycarbonyl, and X and X' are both ethylene with the appropriate compound of formula XXX as defined in Table 4, followed by acid hydrolsis with, for example, trifluoroacetic acid.

TABLE 4

| XXX | For Example No. |
|---|---|
| ![pyrido-oxazinedione] | 5, 8, 11, 14, 17, 20, 24, 27 |

3) Compounds of Formula VI

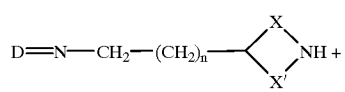 XIV

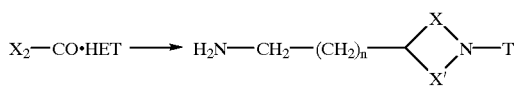 VI

These compounds may be prepared by acid hydrolysis, with, for example, aqueous potassium hydrogen sulphate solution, of the product of the reaction of the compound of formula XIV, in which D is a protecting group, for example benzylidene, with the appropriate compound of formula $X_2$-CO.HET as defined in Table 5.

TABLE 5

| $X_2$-CO.HET | For Example No. |
|---|---|
| ![pyridine-2-COOH] | 28 |
| ![pyridine-3-COCl] | 29 |
| ![2-Cl-pyridine-3-COOH] | 30, 31 |

4) Compounds of Formula XVI

Compounds of formula XVI in which R" is H or $CO_2Et$ may be prepared by cyclisation of the appropriate compound of formula XIX in the presence of potassium carbonate.

Compounds of formula XVI in which R" is $CO_2H$ may be prepared by hydrolysis of the corresponding compound of formula XVI in which R" is $CO_2Et$.

Compounds of formula XVI in which R" is H may also be prepared by decarboxylation of the corresponding compound of formula XVI in which R" is $CO_2H$.

Compounds of formula XVI in which R" is $CONH_2$ may be prepared by amination of the corresponding compound of formula XVI in which R" is $CO_2Et$.

Compounds of formula XVI in which R" is $CONMe_2$ may be prepared by amination of the corresponding compound of formula XVI in which R" is $CO_2Et$.

Compounds of formula XVI in which R" is CHO may be prepared by reduction of the corresponding compound of formula XVI in which R" is $CO_2Et$.

Compounds of formula XVI in which R" is COMe may be prepared by reaction of the corresponding compound of formula XVI in which R" is $CO_2H$ with methyl lithium.

Compounds of formula XVI in which R" is CN may be prepared by dehydration of the corresponding compound of formula XVI in which R" is $CONH_2$.

EXAMPLE 32

The use of compounds of the present invention in the manufacture of pharmaceutical compositions is illustrated by the following description. In this description the term "active compound" denotes any compound of the invention but particularly any compound which is the final product of one of the preceding Examples.

a) Capsules

In the preparation of capsules, 10 parts by weight of active compound and 240 parts by weight of lactose are de-aggregated and blended. The mixture is filled into hard gelatin capsules, each capsule containing a unit dose or part of a unit dose of active compound.

b) Tablets

Tables are prepared from the following ingredients.

|  | Parts by weight |
|---|---|
| Active compound | 10 |
| Lactose | 190 |
| Maize starch | 22 |
| Polyvinylpyrrolidone | 10 |
| Magnesium stearate | 3 |

The active compound, the lactose and some of the starch are de-aggregated, blended and the resulting mixture is granulated with a solution of the polyvinyl-pyrrolidone in ethanol. The dry granulate is blended with the magnesium stearate and the rest of the starch. The mixture is then compressed in a tabletting machine to give tablets each containing a unit dose or a part of a unit dose of active compound.

Enteric Coated Tablets

Tablets are prepared by the method described in (b) above. The tablets are enteric coated in a conventional manner using a solution of 20% cellulose acetate phthalate and 3% diethyl phthalate in ethanol:dichloromethane (1:1).

d) Suppositories

In the preparation of suppositories, 100 parts by weight of active compound is incorporated in 1300 parts by weight of triglyceride suppository base and the mixture formed into suppositories each containing a therapeutically effective amount of active ingredient.

What is claimed is:
1. A compound of the formula I

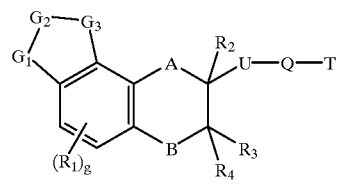

(I)

or an enantiomer thereof, or a pharmaceutically acceptable salt, wherein

A is —O—;

B is —O—;

$G_1$—$G_2$—$G_3$ is —NH—C(R")=CH—, —NH—N=CH— or —NH—CH=N—;

R" is H; an alkyl group containing 1 to 3 carbon atoms optionally substituted by one or more halo; carboxy; an alkanoyl group containing 1 to 6 carbon atoms; an alkoxycarbonyl group in which the alkoxy group contains 1 to 3 carbon atoms; formyl, cyano; or a carbamoyl group or carbamoylmethyl group each optionally N-substituted by one or two alkyl groups each containing 1 to 3 carbon atoms;

g is 0;

$R_2$ is H, an alkyl group containing 1 to 3 carbon atoms, or an alkoxy group containing 1 to 3 carbon atoms;

$R_3$ and $R_4$, which are the same or different are H, or an alkyl group containing 1 to 3 carbon atoms;

U is an alkylene chain containing 1 to 3 carbon atoms, optionally substituted by one or more alkyl groups, each containing 1 to 3 carbon atoms;

Q is a divalent group of formula IIa or IIc

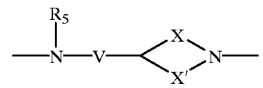

(IIa)

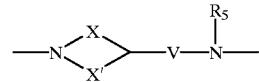

(IIc)

wherein

V is a bond or an alkylene chain containing 1 to 3 carbon atoms optionally substituted by one or more alkyl groups each containing 1 to 3 carbon atoms;

X and X' are ethylene;

$R^5$ is H or an alkyl group containing 1 to 3 carbon atoms; and

T is a group CO-HET wherein

HET is 2-, 3- or 4-pyridyl, which is unsubstituted or substituted by one or more substituents selected from a) halo, b) an alkyl group containing 1 to 3 carbon atoms optionally substituted by one or more halo, c) an alkoxy group containing 1 to 3 carbon atoms optionally substituted by one or more halo, d) an alkylthio group containing 1 to 3 carbon atoms optionally substituted by one or more halo, e) hydroxy, f) an acyloxy group containing 1 to 3 carbon atoms, g) hydroxymethyl, h) cyano, i) an alkanoyl group containing 1 to 6 carbon atoms, j) an alkoxycarbonyl group containing 2 to 6 carbon atoms, k) a carbamoyl group or carbamoylmethyl group each optionally N-substituted by one or two alkyl groups each containing 1 to 3 carbon atoms, l) a sulphamoyl or sulfamoylmethyl group each optionally being N-substituted by one or two alkyl groups each containing 1 to 3 carbon atoms, m) an amino group optionally substituted by one or two alkyl groups each containing 1 to 5 carbon atoms, n) 1-pyrrolidinyl and 1-piperidinyl.

2. The compound of formula I defined in claim 1, wherein R″ is H, $CO_2Et$, $CONH_2$, $CONMe_2$, COMe, CN, or CHO.

3. The compound of formula I defined in claim 1, wherein $R_2$ is hydrogen.

4. The compound of formula I defined in claim 1, wherein $R_3$ and $R_4$ are hydrogen.

5. The compound of formula I defined in claim 1, wherein HET is 2-pyridyl, 3-pyridyl, 3-(2-amino)pyridyl, or 3-(2-methoxy)pyridyl.

6. The compound of formula I defined in claim 1, wherein $G_1$—$G_2$—$G_3$ is —NH—CH=CH—, $R_2$ is H or an alkyl group containing 1 to 3 carbon atoms, $R_3$ and $R_4$, which are the same or different, are H or methyl, U is methylene, V is methylene or ethylene, $R_5$ is H or methyl, and T is the group CO-HET in which HET is 2-, 3- or 4-pyridyl optionally substituted by one or more substituents selected from methoxy, trifluoromethyl, halo or an amino group optionally substituted by one or two alkyl groups each containing 1 to 3 carbon atoms.

7. The compound of formula I defined in claim 1, selected from the group consisting of:

2-Amino-N-{[1-(2,3-dihydro-7H-1,4-dioxino[2,3-e]indol-2-ylmethyl)-4-piperidiyl]methyl}-pyridine-3-carboxamide;

N-{[1-(2,3-dihydro-7H-1,4-dioxino[2,3-e]indol-2-ylmethyl)-4-piperidiyl]methyl}-pyridine-2-carboxamide;

Ethyl 2,3-dihydro-2-({4-[(2-pyridinecarboxamido)methyl]piperidino}methyl)-7H-1,4-dioxino[2,3-e]indole-8-carboxylate;

Ethyl 2,3-dihydro-2-({4-[(3-pyridinecarboxamido)methyl]piperidino}methyl)-7H-1,4-dioxino[2,3-e]indole-8-carboxylate;

Ethyl 2-({4-[(2-amnino-3-pyridinecarboxamido)methyl]piperidino}methyl )-2,3-dihydro-7H-1,4-dioxino[2,3-e]indole-8-carboxylate;

2,3-Dihydro-2-({4-[(2-pyridinecarboxamido)methyl]piperidino}methyl)-7H-1,4-dioxino[2,3-e]indole-8-carboxamide;

2,3-Dihydro-2-({4-[(3-pyridinecarboxamido)methyl]piperidino}methyl)-7H-1,4-dioxino[2,3-e]indole-8-carboxamide;

2-({4-[(2-Amino-3-pyridinecarboxamido)methyl]piperidino}methyl)-2,3-dihydro-7H-1,4-dioxino [2,3-e]indole-8-carboxamide;

2,3-Dihydro-N,N-dimethyl-2-({4-[(2-pyridinecarboxamido)methyl]piperidino}methyl)-7H-1,4-dioxino[2,3-e]indole-8-carboxamide;

2,3-Dihydro-N,N-dimethyl-2-({4-[(3-pyridinecarboxamido)methyl]piperidino}methyl)-7H-1,4-dioxino[2,3-e]indole-8-carboxamide;

2-({4-[(2-Amino-3-pyridinecarboxarnido)methyl]piperidino}methyl)-2,3-dihydro-N,N-dimethyl-7H-1,4-dioxino[2,3-e]indole-8-carboxamide;

N-{[1-(8-Acetyl-2,3-dihydro-7H-1,4-dioxino[2,3-e]indol-2-ylmethyl)-4-piperidyl]methyl}pyridine-2-carboxarnide;

N-{[1-(8-Acetyl-2,3-dihydro-7H-1,4-dioxino [2,3-e]indol-2-ylmethyl)-4-piperidyl]methyl}pyridine-3-carboxamide;

N-{[1-(8-Acetyl-2,3-dihydro-7H-1,4-dioxino [2,3-e]indol-2-ylmethyl)-4-piperidyl]methyl}-2-aminopyridine-3-carboxamnide;

N-{[1-(8-Cyano-2,3-dihydro-7H-1,4-dioxino[2,3-e]indol-2-ylmethyl)-4-piperidyl]methyl}pyridine-2-carboxamide;

N-{[1-(8-Cyano-2,3-dihydro-7H-1,4-dioxino [2,3-e]indol-2-ylmethyl)-4-piperidyl]methyl}pyridine-3-carboxamnide;

2-Amino-N-[1-{8-cyano-2,3-dihydro-7H-1,4-dioxino[2,3-e]indol-2-ylmethyl)-4-piperidyl]methyl}pyridine-3-carboxamide;

N-{[1-(8-Formyl-2,3-dihydro-7H-1,4-dioxino[2,3-e]indol-2-ylmethyl)-4-piperidyl]methyl}pyridine-2-carboxamide;

N-{[1-(8-Formyl-2,3-dihydro-7H-1,4-dioxino[2,3-e]indol-2-ylmethyl)-4-piperidyl]methyl}pyridine-3-carboxamide;

2-Amino-N-{[8-formyl-2,3-dihydro-7H-1,4-dioxino[2,3-e]indol-2-ylmethyl)-4-piperidyl]methyl}pyridine-3-carboxamide;

N-{[1-(2,3-Dihydro-7H-1,4-dioxino[2,3-e]indol-2-ylmethyl)-4-piperidyl]methy}-2-methoxypyridine-3-carboxamide;

N-{[1-(2,3-Dihydro-7H-1,4-dioxino[2,3-e]indazol-2-ylmethyl)-4-piperidyl]methyl}pyridine-2-carboxamide;

N-{[1-(2,3-Dihydro-7H-1,4-dioxino[2,3-e]indazol-2-ylmethyl)-4-piperidyl]methyl}pyridine-3-carboxamide;

2-Amino-N-{[1-(2,3-dihydro-7H-1,4-dioxino[2,3-e]indazol-2-ylmethyl)-4-piperidyl]methyl}pyridine-3-carboxamide;

N-{[1-(2,3-Dihydro-7H-1,4-dioxino[2,3-e]benzimidazol-2-ylmethyl)-4-piperidyl]methyl}pyridine-2-carboxamide;

N-{[1-(2,3-Dihydro-7H-1,4-dioxino[2,3-e]benzimidazol-2-ylmethyl)-4-piperidyl]methyl}pyridine-3-carboxamide;

2-Amino-N-{[1-(2,3-dihydro-7H-1,4-dioxino[2,3-e]benzimidazol-2-ylmethyl)-4-piperidyl]methyl}pyridine-3-carboxamide;

2,3-Dihydro-2-(N-{[1-(2-pyridylcarbonyl)-4-piperidyl]methyl}aminomethyl)-7H-1,4-dioxino[2,3-e]indole;

2,3-Dihydro-2-(N-{[1-(3-pyridylcarbonyl)-4-piperidyl]methyl}aminomethyl)-7H-1,4-dioxino[2,3-e]indole;

2-(N-{[1-(2-Amino-3-pyridylcarbonyl)-4-piperidyl]methyl}aminomethyl)-2,3-dihydro-7H-1,4-dioxino[2,3-e]indole; and 2-(N-{[1-(2-Chloro-3-pyridylcarbonyl)-4-piperidyl]methyl}aminomethyl)-2,3-dihydro-7H-1,4-dioxino[2,3-e]indole;

and pharmaceutically acceptable salts thereof in the form of individual enantiomers, racemates, or other mixtures of enantiomers.

8. The compound of formula I defined in claim 7, which is (S)-2-amino-N-{[1-(2,3-dihydro-7H-1,4-dioxino[2,3-e]indol-2-ylmethyl)-4-piperidyl]methyl}pyridine-3- carboxamide; or (S)-N-{[1-(2,3-dihydro-7H-1,4-dioxino[2,3-e]indol-2-ylmethyl)-4-piperidyl]methyl}pyridin-2-carboxamide.

9. The compound of formula I defined in claim 1, wherein R" is H, $CO_2Et$, $CONH_2$, $CONMe_2$, COMe, CN, or CHO; $R_2$, $R_3$ and $R_4$ are hydrogen; U is methylene; V is methylene; and T is a group CO-HET wherein HET denotes 2-pyridyl, 3-pyridyl, 3-(2-amino)pyridyl, or 3-(2-methoxy)pyridyl.

10. The compound of formula I defined in claim 1, wherein U is methylene.

11. The compound of formula I defined in claim 1, wherein U is methylene and Q is of the formula IIc.

12. The compound of formula I defined in claim 1, wherein Q is of the formula IIc.

13. The compound of formula I defined in claim 9, wherein Q is of the formula IIc.

14. The compound of formula I defined in claim 1, wherein $G_1$—$G_2$—$G_3$ denotes —NH—C(R")=CH—.

15. The compound of formula I defined in claim 9, wherein $G_1$—$G_2$—$G_3$ denotes —NH—C(R")=CH—.

16. The compound of formula I defined in claim 1, wherein Q is of the formula IIc, and $G_1$—$G_2$—$G_3$ denotes —NH—C(R")=CH—.

17. The compound of formula I defined in claim 9, wherein Q is of the formula IIc, and $G_1$—$G_2$—$G_3$ denotes —NH—C(R")=CH—.

18. The compound of formula I defined in claim 9, wherein U is methylene, V is methylene and Q is of the formula IIc.

19. A pharmaceutical composition comprising a therapeutically effective amount of a compound of formula I or a salt thereof as defined in claim 1, and a pharmaceutically acceptable diluent or carrier.

20. The pharmaceutical composition defined in claim 19, wherein U is methylene, V is methylene and Q is of the formula IIc.

21. A method for treating depression, anxiety, psychoses, tardive dyskinesia, Parkinson's disease, obesity, hypertension, Tourette's syndrome, sexual dysfunction, drug addiction, drug abuse, cognitive disorders, Alzheimer's disease, senile dementia, obsessive-compulsive behaviour, panic attacks, social phobias, eating disorders and anorexia, cardiovascular and cerebrovascular disorders, non-insulin dependent diabetes mellitus, hyperglycaemia, constipation, arrhythmia, disorders of the neuroendocrine system, stress, prostatic hypertrophy, or spasticity in human beings which comprises the administration of a therapeutically effective amount of a compound of formula I as defined in claim 1, to a patient in need thereof.

22. The method defined in claim 21, wherein U is methylene, V is methylene and Q is of the formula IIc.

23. A process for the preparation of a compound of formula I as defined in claim 1, wherein Q is a group of formula IIc, comprising the reaction of a compound of formula VII

VII

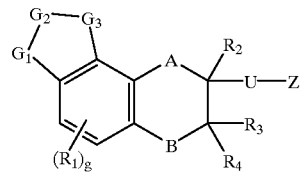

wherein Z is a leaving group, with a compound of formula XXXV

XXXV

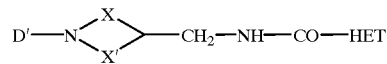

wherein D' is hydrogen, optionally in the presence of a base.

* * * * *

UNITED STATES PATENT AND TRADEMARK OFFICE
CERTIFICATE OF CORRECTION

PATENT NO.: 6,107,310

DATED: August 22, 2000

INVENTOR(S): BIRCH et al.

It is certified that error appears in the above-identified patent and that said Letters Patent is hereby corrected as shown below:

On the cover page, item [57], line 17, "mrellitus, hyperglvcaemia," should be --mellitus, hyperglycaemia,--.

Col. 29, claim 7, line 47, "piperidino}methyl )" should be --piperidino}methyl)--.

Col. 30, claim 7, line 3, "carboxarnide" should be --carboxamide--.

Col. 30, claim 7, line 16, "carboxamnide" should be --carboxamide--.

Signed and Sealed this

Twenty-ninth Day of May, 2001

Attest:

NICHOLAS P. GODICI

*Attesting Officer*   *Acting Director of the United States Patent and Trademark Office*